United States Patent [19]

DePrince et al.

[11] Patent Number: 5,008,112

[45] Date of Patent: Apr. 16, 1991

[54] DEVICE FOR THE EXTENDED DELIVERY OF DIFFUSIBLE AGENTS

[75] Inventors: Randolph B. DePrince; Ravi Viswanathan, both of Terre Haute, Ind.

[73] Assignee: International Minerals & Chem. Corporation, Northbrook, Ill.

[21] Appl. No.: 809,437

[22] Filed: Dec. 16, 1985

[51] Int. Cl.$^5$ .............................................. A61K 9/22
[52] U.S. Cl. .................................... 424/468; 424/477
[58] Field of Search ...................... 424/28, 422–424, 424/427, 430, 451–453, 455, 457, 458, 460, 461, 462, 468, 473, 477, 479; 604/890–893

[56] References Cited

U.S. PATENT DOCUMENTS

| | | | |
|---|---|---|---|
| 1,815,902 | 7/1931 | Ellzey | 424/453 |
| 3,279,996 | 10/1966 | Long et al. | |
| 3,538,214 | 11/1970 | Polli et al. | 424/19 |
| 3,845,770 | 11/1974 | Theeuwes et al. | |
| 3,929,132 | 12/1975 | Higuchi | |
| 3,982,536 | 9/1976 | Krogseng et al. | |
| 3,993,072 | 11/1976 | Zaffaroni | |
| 3,993,073 | 11/1976 | Zaffaroni | 604/891 |
| 4,210,139 | 7/1980 | Higuchi | 604/892 |
| 4,278,087 | 7/1981 | Theeuwes et al. | 128/127 |
| 4,298,003 | 11/1981 | Theeuwes et al. | 604/892 |
| 4,320,759 | 3/1982 | Theeuwes | |
| 4,439,181 | 3/1984 | Blackshear et al. | |
| 4,439,196 | 3/1984 | Higuchi | 604/890 |
| 4,455,143 | 6/1984 | Theeuwes et al. | 604/890 |
| 4,475,916 | 10/1984 | Himmelstein | |

FOREIGN PATENT DOCUMENTS

| | | | |
|---|---|---|---|
| 2524311 | 10/1983 | France | 424/453 |
| WO83/03061 | 9/1983 | PCT Int'l Appl. | 424/452 |

Primary Examiner—C. Fred Rosenbaum
Assistant Examiner—Sharon Rose
Attorney, Agent, or Firm—Wendell Ray Guffey; Thomas L. Farquer

[57] ABSTRACT

A device for the continuous administration of a diffusible agent having a relatively rapid rate of diffusion and a diffusible agent having a relatively show rate of diffusion comprises:

a wall, formed at least in part by a porous membrane, which surrounds and defines a reservoir, the reservoir comprising:

(a) a compartment which comprises the agent having the relatively slow rate of diffusion, wherein said compartment is in direct contact with the porous membrane part of the wall and (b) at least one compartment which comprises the agent having the relatively rapid rate of diffusion, wherein said compartment is not in direct contact with the porous membrane part of the wall and is separated from the compartment comprising the agent having the relatively slow rate of diffusion by a porous partition, such that when said device is exposed to said fluid medium, said agents will diffuse through the porous membrane part of said wall at a substantially steady rate for a prolonged period of time.

38 Claims, 3 Drawing Sheets

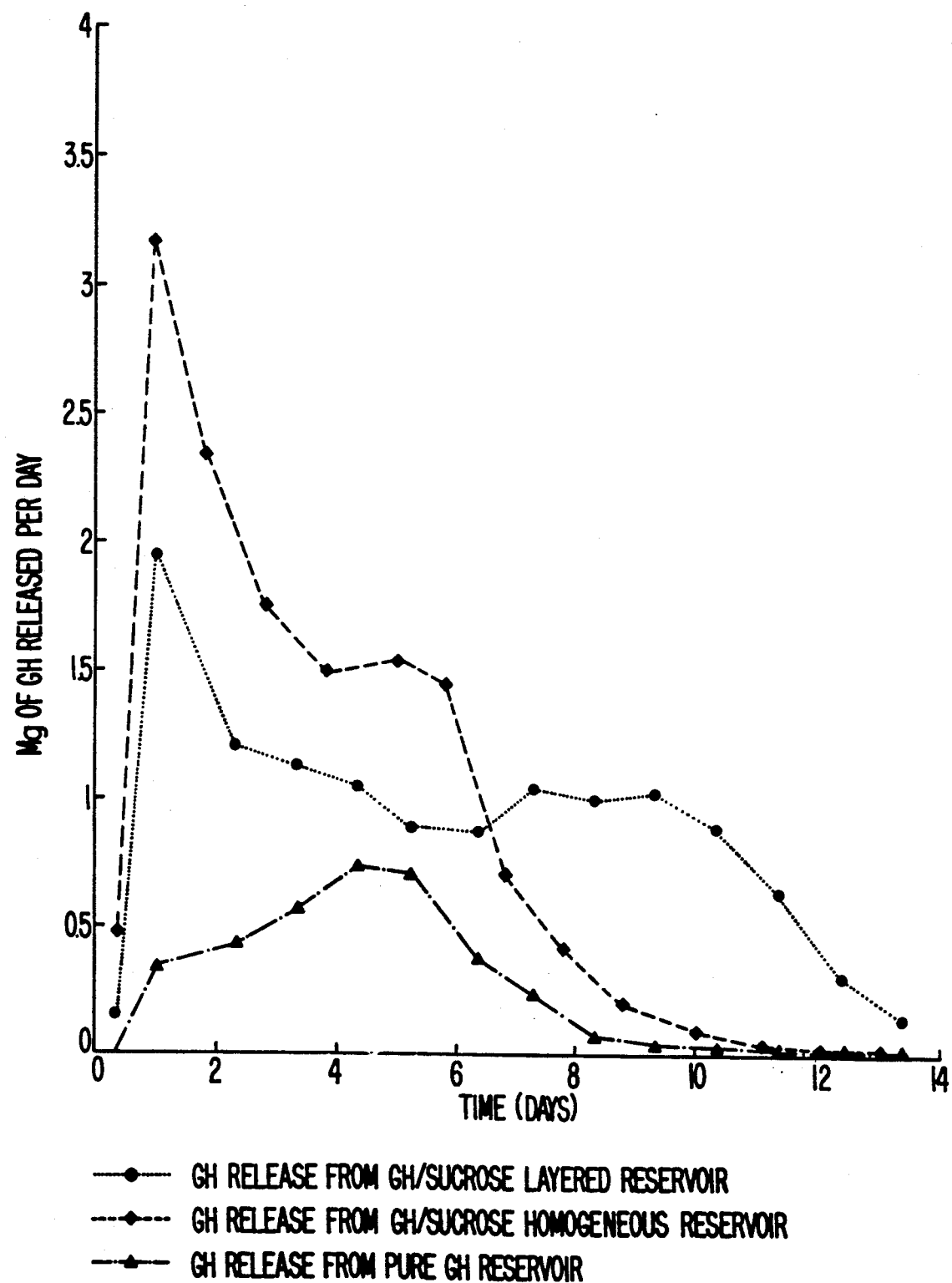

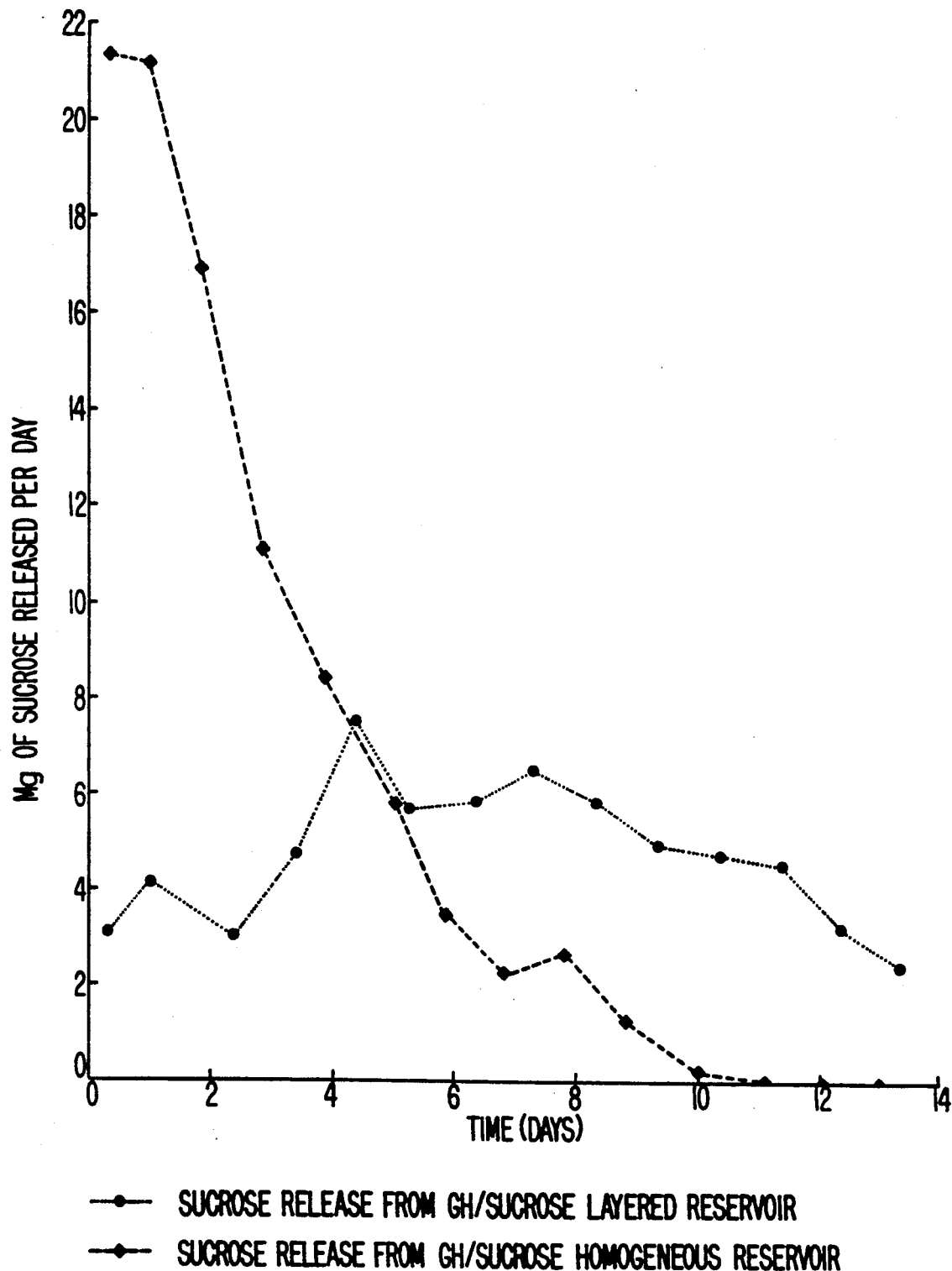

DEVICE FOR THE EXTENDED DELIVERY OF DIFFUSIBLE AGENTS

FIELD OF THE INVENTION

This invention relates to a device for the delivery by diffusion of at least two agents into a fluid medium at a substantially steady rate. More particularly, this invention relates to such a device wherein the agents to be delivered have different rates of diffusion.

BACKGROUND OF THE INVENTION

A variety of devices have been disclosed in the art which provide for the release of an agent, into a fluid medium over a prolonged period of time. Often the agent is a beneficial agent, such as a drug or medicament, which is to be released in the body of a living being. For example, U.S. Pat. No. 3,279,996, issued to Long et al., discloses a method and means for the controlled release of a therapeutic agent into a living organism by implanting within the body of that organism a capsule formed of silicone rubber and containing a therapeutic agent soluble in the rubber and capable of diffusing through the rubber to its outer surface at a constant rate. U.S. Pat. No. 3,993,072, issued to Zaffaroni, discloses a device which comprises a wall surrounding a reservoir containing a drug. The reservoir contains a solid drug carrier which contains the drug of interest. The wall is formed of a microporous material having a plurality of micropores and formed with diffusional conduits throughout. The pores of the wall contain a drug release rate controlling medium which is also permeable to the drug. Another patent, U.S. Pat. No. 3,845,770, issued to Theeuwes et al., is directed to an osmotic device for the controlled release of an agent which comprises a semi-permeable membrane that surrounds a compartment which contains the agent. The wall is permeable to an external body fluid but impermeable to the agent and has a passageway for delivering the agent to the body. To release the agent, fluid is imbibed through the wall into the compartment to produce a solution of the agent. That solution is dispensed through the passageway at a rate controlled by the permeability of the wall and the osmotic pressure gradient across the wall of the device.

Also of interest is U.S. Pat. No. 4,320,759, issued to Theeuwes, which discloses a device which comprises a microporous wall which surrounds a compartment having a space which contains a beneficial agent separated by a partition from a space which contains an expandable entity, either a swellable polymer or an osmotically effective solute. With this device, an agent is delivered by fluid diffusing through the microporous wall into the space containing the expandable entity causing that space to swell and expand against the partition, urging it to move into the other compartment and maintain the agent in a saturated state. The agent diffuses through fluid-filled paths in the microporous wall.

Despite these and various other systems and devices for releasing beneficial agents, certain problems have remained. For instance, there are times when it would be desirable to deliver two or more agents together from the same device. If the two agents have different rates of diffusion through the porous membrane of the device, however, the delivery can be difficult to effect, especially if it also is desired that the delivery extend over a prolonged period of time.

For example, certain beneficial agents, such as some proteins, when placed in conventional delivery systems, tend to form insolubles and lose their bioactivity upon extended exposure to aqueous environments. In U.S. Pat. No. 4,439,181, issued to Blackshear, the disclosure was made that in some instances precipitation of a protein (insulin in this instance) within the delivery system can be prevented, or at least substantially decreased, by adding an effective amount of a compound that solubilizes the protein and inhibits the action of precipitation agents.

More recently, commonly assigned U.S. Pat. No. 4,816,568 discloses the stabilization of growth hormone by adding various low molecular weight stabilizers. It has been found that a mixture of the stabilizer and growth hormone can be pelletized, placed in a slow release diffusion delivery device, and used as an implant. Further improvements are sought in this system, however, for the stabilizing additive, having a much smaller molecular weight and size than the protein, has a tendency to diffuse out of the device at a much faster rate than the protein. Once the additive is gone, the protein again is subject to wetting problems and aggregation.

There thus remains a need for a device that can deliver for a sustained period of time two or more agents which have different rates of diffusion. It furthermore would be beneficial to have such a device capable of releasing the agents at a substantially steady rate over time.

Accordingly, it is an object of this invention to provide a delivery device for dispensing agents into a fluid medium which overcomes the disadvantages found in devices of the prior art.

It also is an object of the present invention to provide such a device wherein the rate of release of the agents approaches zero order and the agents are released over a prolonged period of time.

It is a further object of this invention to provide such a delivery system in a variety of sizes and shapes and in form suitable for placement within the body of a living being, as by oral ingestion, implantation into body tissues or insertion into a body cavity.

Additional objects of the present invention shall become apparent to those skilled in the art from the description of the invention below taken in conjunction with the accompanying claims and figures.

SUMMARY OF THE INVENTION

In accordance with the present invention, there is disclosed a device for the continuous administration in a fluid medium of a diffusible agent having a relatively rapid rate of diffusion and a diffusible agent having a relatively slow rate of diffusion which comprises: a wall, formed at least in part by a porous membrane, which surrounds and defines a reservoir, the reservoir comprising (a) a compartment which comprises the agent having a relatively slow rate of diffusion through the porous membrane, the compartment in direct contact with the porous membrane part of the wall, and (b) at least one compartment which comprises an agent having a relatively rapid rate of diffusion through the porous membrane, wherein the compartment is not in direct contact with the porous membrane part of the wall and is separated by a porous partition from the compartment comprising the agent having the relatively slow rate of diffusion, such that when said device is exposed to said fluid medium, said agents will diffuse through the porous membrane part of said wall at a substantially steady rate for a prolonged period of time.

This invention also relates to a method of continuously administering at least two agents into a fluid medium.

BRIEF DESCRIPTION OF THE DRAWINGS

FIG. 4 is a graph which illustrates the average amount of porcine growth hormone (pGH) (slow diffusing, active agent) released daily from devices in accordance with this invention. The devices (labelled Layered Reservoir) have two compartments, one containing a mixture of pGH and sucrose and one containing sucrose. The compartments are separated from one another by a microporous polyethylene disc. The graph also illustrates the release from devices containing a homogeneous mixture of growth hormone and sucrose (labelled Homogeneous Reservoir) and from devices containing only growth hormone (labelled pure GH Reservoir). The daily release of sucrose (rapidly diffusing, stabilizing agent) from the Layered and Homogeneous Reservoir devices is illustrated in FIG. 5.

FIG. 5 is a graph which illustrates the average amount of sucrose (rapid diffusing and stabilizing agent) released per day from devices in accordance with this invention. The devices (labelled Layered Reservoir) have two compartments, one containing a mixture of pGH and sucrose and one containing sucrose The compartments are separated from one another by a microporous polyethylene disc. The graph also illustrates the release from devices containing a homogeneous mixture of growth hormone and sucrose (labelled Homogeneous Reservoir). The daily release of growth hormone (slow diffusing and active agent) from the Layered and Homogeneous Reservoir devices is illustrated in FIG. 4.

DETAILED DESCRIPTION OF THE INVENTION

Figure 1:
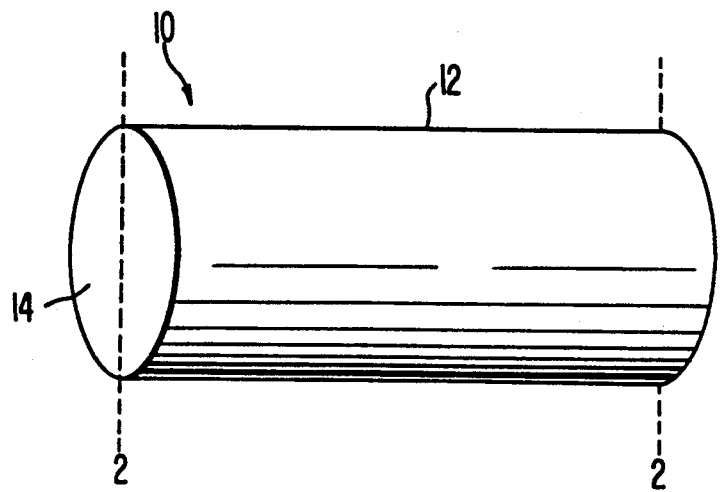
FIG. 1 depicts a delivery device of this invention designed and shaped for placement within the body of a living being, which contains a relatively rapidly diffusing agent and a relatively slowly diffusing agent.

The devices of this invention will be described below primarily in terms of devices for the delivery of agents in the body of a living being. It is to be understood, however, that this is for illustrative purposes only, and that the devices are equally suited to the administration of different types of diffusible agents into a variety of fluid mediums.

There are a number of situations wherein it may be desirable to place two or more diffusible agents in one delivery device. As noted above, one such situation occurs when the agent of interest forms insolubles when it comes in contact with the fluid medium in the absence of a stabilizing agent. This type of situation can occur, for example, when the agent of interest is a high molecular weight, hydrophobic polypeptide such as insulin or an animal growth hormone.

There also may be times when it may be desirable to place two or more beneficial agents in one delivery device. For purposes of this application, "beneficial agent" is defined as an agent that produces a useful effect in the environment in which it is released either at a site in close proximity to its point of release or at a site removed from the release site. When the device of this invention is to be placed in the body of a living being, the term beneficial agent includes, but is not limited to, drugs, vitamins, nutritional supplements, and biologically active proteins. The term "drug" includes hypnotics and sedatives, tranquilizers, anti-convulsants, muscle relaxants, analgesics, anti-inflammatory agents, local anesthetics, antimicrobials, androgenic, progestational and estrogenic steroids, sympathomimetric drugs and diuretics. The beneficial agent may be present as a pharmacologically acceptable derivative that lends itself to passage through the body in a body fluid and can be converted to the active agent within the body through the action of body enzymes-assisted transformation, pH, activity by a specific organ, or other similar action. The term "agent", as used throughout this application, refers to beneficial agents as well as other types of compounds which may be present in the delivery devices, including, for example, stabilizers and chelating agents.

A third type of diffusion device comprising two or more agents comprises a beneficial agent and an agent which can act in some way to promote the rate of release of that beneficial agent. For example, the beneficial agent may be present in the form of a metal complex and thus have a lower solubility than it would if present in un-complexed form. The addition of a chelating agent to the device will liberate the beneficial agent, thereby increasing the beneficial agent's solutibility and, thus, its release rate from the delivery device.

As noted above, these and other similar devices are of only limited usefulness if the agents present in the device have different rates of diffusion. This invention overcomes this problem by providing novel devices for the sustained release of two or more such agents into a fluid medium at a substantially steady rate over a prolonged period of time.

The rate of diffusion of any compound is a function of both its molecular weight and its solubility in the fluid of interest. For purposes of illustration of the present invention, agents present in the novel delivery devices will be described as having a "relatively rapid" rate of release or diffusion or a "relatively slow" rate of release or diffusion. These terms are intended only as providing a point of comparison between the agents when they are mixed together and allowed to diffuse through the walls of a delivery device.

Accordingly, the delivery devices of the present invention provide a means for diffusing a diffusible agent having a relatively rapid diffusion rate and a diffusible agent having a relatively slow diffusion rate at a substantially steady rate for a prolonged period of time. A device made in accordance with this invention comprises a wall, formed at least in part by a porous membrane, which surrounds and defines a reservoir, the reservoir comprising:

(a) a compartment which comprises the agent having the relatively slow rate of diffusion, wherein said compartment is in direct contact with the porous membrane part of the wall and (b) at least one compartment which comprises the agent having the relatively rapid rate of diffusion, wherein said compartment is not in direct contact with the porous membrane part of the wall and is separated by a permeable partition from the compartment comprising the agent having the relatively slow rate of diffusion, such that when said device is exposed to said fluid mediuim, said agents will diffuse through the porous membrane part of the wall at a substantially steady rate for a prolonger period of time.

Applicants have discovered that by constructing the delivery device in this manner, such that the agent having a relatively rapid rate of diffusion has to pass through an internal permeable partition, the porosity of which can be varied, as well as through the porous portion of the external wall of the device, its diffusion rate can be slowed and controlled much more efficiently than if the two agents are simply mixed homogeneously within the device. As a result, the life of the device—that period of time in which the two agents are released together—can be extended.

A variety of materials can be used to make the porous partition which separates the two agents. Any material which is inert, can be formed into a wall or partition, is compatible with the agents placed in the device, and is permeable to the agent having the relatively rapid rate of diffusion may be used. If the device is one which will be placed in the body of a living being, the material which forms the permeable partition also desirably is one which is suited for inclusion in such a device.

Materials suitable for forming the partition include naturally occurring and synthetic materials known in the art having a plurality of fused particles which provide a supporting structure having microscopic sized interconnecting pores. A variety of such materials are commercially available or can be made by different methods known in the art, including etched nuclear track, leaching, polyelectrolytic processes, ion exchange polymer reactions and other techniques. See, for example, *Synthetic Polymer Membranes*, R. E. Kesting, Chapters 4 and 5, published by McGraw-Hill, 1971; and *Chemical Reviews: Ultrafiltration* 18: 373–455 (1934).

Microporous materials useful for making these partitions include microporous polyalkylenes, such as microporous polyethylene, microporous polycarbonates, microporous polyamides, microporous modacrylic copolymers, polyesters prepared by esterification of a dicarboxylic acid or anhydride with an alkylene polyol, phenolic polyesters, cross-linked olefin polymers, polyolefins, polyurethanes, polyimides and polybenzimidazoles. Microporous polyethylene is a preferred microporous material. The actual material chosen will depend upon a variety of factors, including the agent to be placed in the compartment behind the partition, its rate of diffusion through the materials, and the impact desired on the rate of diffusion of the agent from the device into the fluid medium in which the device will be placed.

In addition to the partition, the devices of this invention also comprise an outer wall, at least a portion of which, is a porous membrane. The materials suitable for forming the porous part of this wall are those through which the relatively rapidly diffusing agent and the relatively slowly diffusing agent can pass. Suitable materials are those having essentially the same features and characteristics as those materials suitable for the partition described above, i.e., biological compatibility with the agents and the fluid medium, insolubility in the fluid medium, and, when the device is one which will be placed within the body of a living being, biocompatibility with body fluids (tissue juices, tear fluids, water and the like), tissues and organs. The use of materials soluble in the fluid medium is undesirable, since dissolution of the wall of the device would affect both the rate of release of the agents and the ability of the device to remain in place for prolonged periods of time. The material also desirably is characterized by constant porosity; if the porosity changes over time the rate of release of the agents also will change over time.

Suitable microporous materials for making this part of the devices of this invention include those microporous polymers listed above as suitable partition materials. The porous membrane portion of the reservoir wall can, but need not necessarily, be the same material used to construct the inner partition.

In certain embodiments of the devices of this invention, only a portion of the external wall comprises a porous material. The remainder of the wall comprises a material that is essentially impermeable to the agents and contained in the reservoir and to the fluid medium in which the device will be placed. This portion of the external wall desirably is characterized much as the porous part of the wall was characterized above. The material should be compatible with the fluid medium, and can comprise materials which are commercially available or can be made by processes known in the art. Suitable impermeable materials include acyl substituted cellulose acetates and alkyl derivatives thereof; partially and completely hydrolyzed alkylene-vinyl acetate copolymers; unplasticized polyvinyl acetate; crosslinked homo- and copolymers of polyvinyl acetate; crosslinked polyesters of acryl and methacrylic acid; polyvinyl alkyl ethers, polyvinyl fluoride; silicone; polycarbonates; polyurethane; polyamides; polysulphones; polyimides; polyolefins, polybenzimidazoles; styrene acrlonitrile copolymers; crosslinked poly (ethylene oxide); poly(alkylenes); poly(vinyl imidazole); poly(esters); chlorosulphonated polyolefins; and ethylene-vinyl ester copolymers such as ethylene-vinyl acetate.

The devices of the present invention can be constructed in a variety of shapes, forms and sizes. For example, in one embodiment the reservoir is constructed such that the internal permeable partition reaches from one side of the wall of the reservoir to another, dividing the reservoir into two parts which abut one another. One part comprises the compartment which comprises the agent having the relatively rapid rate of diffusion, the other, the compartment comprising the agent having the relatively slow rate of diffusion. In such an embodiment, only a portion of the wall of the reservoir comprises a porous membrane, and this portion of the wall is in direct contact only with the compartment containing the more slowly diffusing agent; the part of the wall which with the partition defines the compartment comprising the more rapidly diffusing agent, comprises a non-porous, impermeable material.

In another embodiment of the invention, the compartment comprising the agent having the relatively rapid rate of diffusion is completely within the compartment comprising the agent having the relatively slow rate of diffusion, and its boundaries are defined wholly by the partition, which encircles it, and not by the external wall of the reservoir. Such a device is exemplified, for example, by a sphere, the core of which comprises the compartment having the relatively rapidly diffusing agent. This compartment is defined by a permeable partition. Surrounding this core, and comprising the remaining portion of the sphere, is the compartment containing the relatively slowly diffusing agent. In this embodiment, the external wall of the reservoir, the outer covering of the sphere may be made completely of a porous membrane. The relatively rapidly diffusing agent diffuses through the encircling partition, then the two agents diffuse through the outer spherical wall.

In accordance with the present invention, a delivery device may comprise only one compartment comprising the agent having a relatively rapid diffusion rate or it may comprise a plurality of such compartments. In this latter embodiment, the compartments may be in the form of microcapsules, each of which is surrounded by a porous partition which separates the agent having a relatively rapid rate of diffusion from the agent having a relatively slow rate of diffusion. The agent having the relatively rapid rate of diffusion is formed into small beads or pellets which are coated with a thin layer of a porous material through which the agent can leach over time. The thickness of the coating on the microcapsules can be varied to stagger the amount of time needed for the agent to diffuse through the wall or shell of the capsules and into the compartment containing the relatively slowly diffusing agent.

The materials useful to encapsulate the relatively rapidly diffusing agent are those listed above for the permeable partition, provided they can be deposited around the agent.

The relatively rapidly diffusing agent may be encapsulated by any of the standard techniques known in the art, including coacervation, solvent evaporation process and rotary spray drying. For a review of microencapsulation techniques, see Kirk-Othmer, *Encylopedia of Chemical Technology*, Vol. 13:445–450 (1967).

The microcapsules formed typically have a diameter in the range of about 5 to about 250 microns, with a diameter in the range of about 10 to about 150 microns being preferred.

If desired, additives may be added to the material used to form the wall of the microcapsule. The additives may include binders, fillers, cross-linkers, etc. and may be added to the material before it is formed into the capsule wall or applied to the capsule wall surface. For example, if the encapsulating material forms a rather brittle wall, it may be desirable to add a binder to increase its pliability for ease in handling the microcapsules. Examples of binders which are suitable include sodium bentonite, ethyl cellulose, stearic acid, calcium stearate, adipic acid, fumaric acid, polyethylene glycol and cellulose acetate. Generally, the binder is present in amounts of from about 0.5 to about 10 percent by weight of the weight of the encapsulating material. Preferably, the binder is present in amounts of from 1 to about 5 percent by weight.

The rate of release of the relatively rapidly diffusing agent through the partition (or through the walls of the microcapsules) is a function of a variety of factors, including the thickness of the partition, the particular agent used, and its permeability through the material which comprises the partition. It is within the knowledge of one skilled in the art to adjust these features when making the capsules such that the additive will diffuse through the walls of the capsules for a certain desired, specified period of time. The amount of rapidly diffusing agent is chosen, and the other factors affecting its rate of release are adjusted, such that when the relatively rapidly diffusing agent and the relatively slowly diffusing agent are placed within the reservoir of a device of this invention and the device, in turn, is placed in its environment of use, a continuous supply of the relatively rapidly diffusing agent is available to the relatively slowly diffusing agent for as long as the latter agent continues to diffuse through the porous membrane of the device. By supplying a continuous supply of the relatively rapidly diffusing agent, the desired effect which is produced when the two agents enter the fluid medium outside the device together can be extended. In addition, the length of time in which the agents can be released at a substantially steady rate can be extended; in a reservoir system the rate of release remains substantially constant only for that period of time in which the reservoir remains saturated with the agent. By slowing and controlling more closely the rate of release of the relatively rapidly diffusing agent, the reservoir will remain saturated for a longer period of time.

The relatively rapidly diffusing agent typically is present in the device in an amount that is in excess of the amount of relatively slowly diffusing agent. Although not wishing to be bound by any limitations, the ratio of relatively rapidly diffusing agent to relatively slowly diffusing agent typically ranges from about 1.5:1 to about 10:1.

In certain embodiments of this invention, it may be desirable to add some of the relatively rapidly diffusing agent to the compartment comprising the relatively slowly diffusing agent rather than placing all of the former agent behind the partition (or partitions). If desired, generally up to about one half of the rapidly diffusing agent may be mixed with the other agent rather than being isolated on the other side of the partition. In this way, it is insured that the two agents can diffuse from the device from the time of its initial placement in the fluid medium before the rapidly diffusing agent passes through the permeable partition. This is true, for example, when the relatively slowly diffusing agent is a high molecular weight protein that forms insolubles in body fluids and the relatively rapidly diffusing agent is a compound which stabilizes the protein by decreasing the formation of insolubles and preserving the bioactivity of the protein yet is not deleterious in the body. By placing a mixture of the protein and stabilizer in one compartment and additional stabilizer in the other compartment(s), the protein will be stabilized as soon as the device is brought into contact with body fluid. The stabilizer present in the mixture will diffuse rapidly through the porous membrane of the reservoir wall, but, as it does so, additional stabilizer will diffuse through the partition(s) and stabilize the protein. In this embodiment, the stabilizer placed in the two compartments need not necessarily be the same compound. In a specific example of this embodiment, the relatively slowly diffusing agent can be an animal growth hormone, such as bovine, porcine or avian growth hormone, and the stabilizer(s) can be selected from sucrose, sorbitol, disaccharides, and amino acids such as glycine, glycine HCl and alanine.

In another example of this embodiment, wherein one compartment of the reservoir comprises a mixture of a relatively rapidly diffusing agent and a relatively slowly diffusing agent and the other compartment comprises a relatively rapidly diffusing agent, two different types of relatively rapidly diffusing agents can be used. For example, using an animal growth hormone again as the slowly diffusing agent, a stabilizer can be placed, as before, in the second compartment behind the permeable partition, but in the first compartment an additive is added which decreases the solubility of the growth hormone. Such additives include compounds such as sodium sulfate and ammonium sulfate. When this device is implanted in a living being, initially no growth hormone will diffuse out of the device and into the body due to the presence of the precipitating additive. Over time, however, that additive will diffuse through the porous membrane, and as it does, the stabilizing additive, such as sucrose, will diffuse from the second compartment into the first to take its place. As this happens, the growth hormone will be resolubilized and will begin to diffuse out of the device. This embodiment of the invention is advantageous if it is desired that there be a lag between the time the device is inserted or implanted and the time treatment with the agent begins.

A device of this invention may be constructed in a variety of shapes, depending upon such factors as the environment in which it will be placed, the length of time desired for the life of the device, and the method by which it will be placed in the fluid medium. For example, if the device is to be placed in the body of a living being it should be constructed such that it has no sharp edges or corners that could be harmful or cause discomfort. Suitable devices, for example, may be cylindrical, circular-disc-like, capsule-shaped or spherical. The shape also can vary depending upon whether such a device is to be orally ingested, implanted into body tissues or inserted into a body cavity. Devices constructed for placement in a fluid medium other than a body fluid have fewer limitations on their shape and, in addition to having the shapes described above, can include rectangular or square designs.

To provide for ease in handling, the agent placed in each compartment may be compressed into pellet form in accordance with conventional techniques prior to being placed in the compartments of the reservoir of the delivery device. If the relatively slowly diffusing agent is in the form of microcapsules, the microcapsules are simply mixed with the relatively slowly diffusing agent, then the mixture can be compressed into pellet form. In this embodiment of the invention, a further necessary characteristic of the encapsulating material is that it be amenable to pelleting. A compound that forms a brittle shell, for example, cannot easily be used to make a compression molded pellet.

A variety of conventional pellet excipients may be added to the agents or agent mixtures. Such excipients include binders and lubricants. Suitable binders include those compounds listed above as binders which can be added to the walls of the microcapsules. While the amount of binders may vary, it generally is present in amounts of from about 0.5 to about 10 percent by weight of the total weight of the pellet.

Lubricants are also may be incorporated into the pellet. Examples of suitable lubricants include common water insoluble lubricants such as, for example, magnesium stearate, sodium stearate, calcium stearate, powdered stearate acid, talc, paraffin, cocoa butter, graphite, lycopodium or combinations thereof. Preferably, the lubricant is a fatty acid derivative such as the stearates, including magnesium stearate, sodium stearate, and calcium stearate. While the amount of lubricant may vary, the lubricant is generally present in amounts of from 0.5 to about 10 percent by weight to the total weight of the pellet. Preferably, the lubricant is present in an amount of from about 1 to about 5 percent by weight.

The agents or mixture of agents then are placed in the reservoir to form the device. A delivery device of the invention can be prepared by placing the tableted agents into a sleeve, such as a tube, into which the tablets fit tightly. In this embodiment, the compressed relatively rapidly diffusing agent is placed within the sleeve, followed by a disc of microporous material through which the agent can pass, followed in turn by the tablet of compressed, relatively slowly diffusing agent. A second disc of microporous material then is pressure fitted over that tablet to provide an end wall through which the two agents can pass. The sleeve itself is constructed of nonporous material such as silicone. If one desires to produce a device which releases the agents from two ends, a non-porous disc can be placed into the tube from the opposite end so that it abuts the tablet of relatively rapidly diffusing agent. A second such tablet is placed over the nonporous disc, followed by another microporus disc (partition) and a second tablet comprising the relatively slowly diffusing agent. A microporous disc then is pressure fitted over the exposed end of this last tablet to provide a second releasing wall. The protruding edges of the sleeve then can be trimmed. If one desires to have only one releasing end, the non-porous sleeve is simply sealed at the non-releasing end.

Similarly, if the relatively rapidly diffusing agent and partition are in the form of microcapsules, the microcapsules are mixed with the other agent, then the mixture compressed into tablet form. The tablet can be placed in a sleeve as above and a device having either one or two releasing ends prepared in a manner analogous to that set forth above. These descriptions illustrate but one embodiment of the delivery device of the invention. Variations in the geometry of the device and the arrangement of its elements can be made by the exercise of the routine skill in the art while retaining its function.

Figure 2:
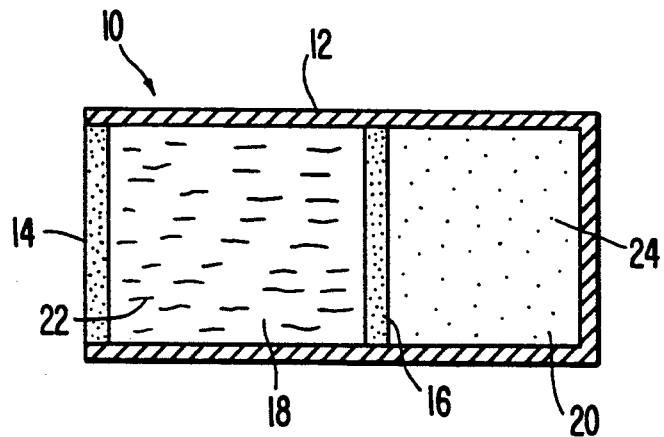
FIG. 2 depicts a cross-sectional view of the device of FIG. 1 which illustrates one embodiment of the invention wherein the device is divided into two compartments by a permeable partition, one compartment comprising the relatively rapidly diffusing agent and the other comprising the relatively slowly diffusing agent.
Figure 3:
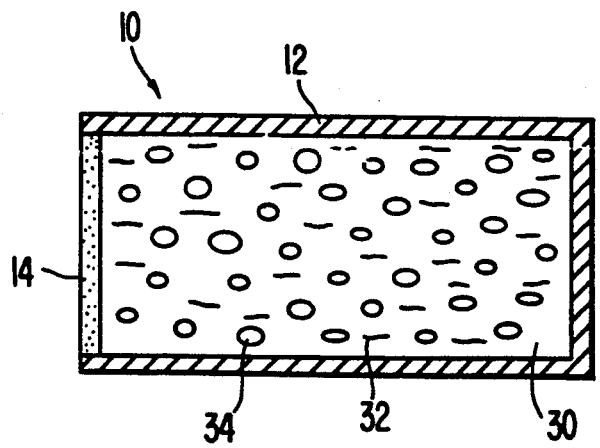
FIG. 3 also depicts a cross-sectional view of the device of FIG. 1, illustrating another embodiment of the invention, wherein the device comprises a plurality of compartments comprising the relatively rapidly diffusing agent. These compartments are in the form of microcapsules, the shells of which comprise permeable partitions.

The devices of this invention are further illustrated in FIGS. 1–3. In FIG. 1, one embodiment of a delivery device of this invention is indicated by the number 10. The device comprises an external wall 12, a portion of which comprises a porous membrane 14. In this embodiment the device is of a size and shape for easy placement and prolonged retention in the body of a living being for the continuous administration of a relatively slowly diffusing agent and a relatively rapidly diffusing agent.

FIGS. 2 and 3 depict possible cross-sections of device 10, cut along the line 2—2 in FIG. 1. FIG. 2 depicts the external wall 12, a portion of which comprises a porous membrane 14. The wall 12 surrounds and defines a reservoir having a permeable partition 16 which separates the reservoir into two compartments, 18 and 20. Compartment 18 comprises a relatively slowly diffusing agent 22, and compartment 20 comprises a relatively rapidly diffusing agent 24.

In an illustration of an alternative embodiment, FIG. 3 also depicts the external wall 12, a portion of which comprises a porous membrane 14. The wall 12 surrounds and defines a reservoir which comprises a mixture 30 of a relatively slowly diffusing agent 32 and a relatively rapidly diffusing agent 34, wherein the agent 34 is in the form of microcapsules.

The device of this invention can be used with a variety of agents. It has been found to be especially useful as a means of delivering certain biologically active proteins, such as an animal growth hormone, that form insolubles and become biologically inactive when they come into contact with body fluids.

The device may be implanted subcutaneously in an animal, or it may be inserted into a body cavity. Alternatively, it can be orally ingested. For example, the device can be employed as a bolus, i.e. a sustained release device which is lodged in the first stomach of a ruminant where it continuously releases beneficial agent.

The delivery devices of the present invention have been described above in terms of certain agents, additives, and structures. It is to be realized, however, that the materials and structures may be varied without departing from the scope and concept of this invention. The invention is further illustrated by the following examples, which are not to be construed as limiting.

EXAMPLE I

Preparation of Extended Delivery Device for Delivery of Porcine Growth Hormone

Parlow pGH (purified porcine growth hormone purchased from A. F. Parlow of the University of California School of Medicine, Harbor General Hospital, Torrence, Calif.) was sieved to a particle range of 250 to 75 microns and mixed by vortexing with sterile sucrose (particle range 250 to 75 micron) in a 2 to 1 ratio. Thirty mg loads of the 2:1 mixture were pelleted on a Key pelletizing machine using a 4 mm die. Seventy mg loads of sterile sucrose also were pelleted on the Key machine using a 4 mm die.

To prepare in vitro implants, a seventy mg sucrose pellet was placed in sterilized silicone tubing (ID 3.2 mm) which had been sealed at one end. Then a 70 micron microporous polyethylene (MPPE) disk (4 mm diameter, 1.5 mm length) was inserted in the tubing until it abutted the sucrose pellet. A thirty mg 2:1 pGH:sucrose pellet then was inserted in the tubing until it abutted the MPPE disk. Then another 70 micron MPPE disk was inserted into the tubing until it abutted the pGH/sucrose pellet to produce a device having one releasing end. This releasing end was trimmed with surgical steel blade, leaving a recessed end of 1.5 mm.

To prepare in vivo implants, two seventy mg sucrose pellets were inserted into sterilized silicone tubing (ID 3.2 mm) with a 4 mm diameter teflon disk between them. Seventy micron MPPE disks (4 mm diameter, 1.5 mm length) then were inserted into each end of the tubing until they abutted the sucrose pellets. Thirty mg 2:1 pGH:sucrose pellets then were inserted into each end of the tubing until they abutted the MPPE disks. Seventy micron MPPE disks then were inserted into each end of the tubing until they abbutted the pGH/sucrose pellets to produce a device with two releasing ends. Each releasing end was trimmed as outlined above.

EXAMPLE II

Administration of Parlow pGH Using an Extended Delivery Device

Using the procedure of Example I for in vitro implants, five layered reservoir devices were prepared. Five first control devices (homogeneous reservoirs) were prepared, each of which contained a homogeneous mixture of Parlow porcine growth hormone and sucrose in a 1:4 ratio. Five second control devices were prepared, each of which contained only Parlow porcine growth hormone. Each of the fifteen devices was placed in a test tube containing 10 mls of PBS with 50 ppm gentamycin sulfate. Release of the porcine growth hormone was measured daily by Bradford assay. Results are set forth below in Tables 1, 2 and 3 and are illustrated in FIG. 4. The release of sucrose from the devices was measured daily by anthrone assay and the results are set forth below in Tables 4 and 5 and FIG. 5. It can be seen in FIG. 4 that the duration of the porcine growth hormone release was extended from the layered reservoir device relative to the first control (homogeneous reservoir) and the second control (pure growth hormone reservoir). It can be seen in FIG. 5 that the duration of the sucrose release from the layered reservoir device was extended relative to the first control (homogeneous reservoir).

TABLE 1

Porcine Growth Hormone Release from Layered Reservoir Devices

| Time (Days) | Milligrams pGH Released Per Day | Cumulative & pGH Released |
| --- | --- | --- |
| 0.33 | 0.15+ −0.05 | 0.25 |
| 1.04 | 1.95+ −0.39 | 7.18 |
| 2.37 | 1.20+ −0.61 | 15.16 |
| 3.39 | 1.13+ −0.25 | 20.92 |
| 4.38 | 1.05+ −0.20 | 26.09 |
| 5.27 | 0.89+ −0.15 | 30.01 |
| 6.38 | 0.87+ −0.11 | 34.84 |
| 7.31 | 1.04+ −0.13 | 39.67 |
| 8.35 | 1.00+ −0.07 | 44.85 |
| 9.36 | 1.02+ −0.07 | 50.00 |
| 10.37 | 0.88+ −0.09 | 54.46 |
| 11.38 | 0.63+ −0.25 | 57.65 |
| 12.39 | 0.30+ −0.18 | 59.15 |
| 13.36 | 0.14+ −0.08 | 59.81 |

TABLE 2

Porcine Growth Hormone Release from First Control (Homogeneous Reservoir)

| Time (Days) | Milligrams pGH Released Per Day | Cumulative % pGH Released |
| --- | --- | --- |
| 0.39 | 0.48+ −0.23 | 0.93 |
| 1.03 | 3.17+ −0.61 | 11.06 |
| 1.89 | 2.34+ −0.28 | 21.13 |
| 2.89 | 1.76+ −0.34 | 29.90 |
| 3.89 | 1.49+ −0.14 | 37.34 |
| 5.06 | 1.54+ −0.18 | 46.36 |
| 5.86 | 1.44+ −0.38 | 52.13 |
| 6.83 | 0.70+ −0.26 | 55.53 |
| 7.82 | 0.42+ −0.18 | 57.59 |
| 8.82 | 0.20+ −0.08 | 58.58 |
| 10.03 | 0.08+ −0.01 | 59.09 |
| 11.11 | 0.04+ −0.02 | 59.30 |
| 12.06 | 0.01+ −0.01 | 59.36 |
| 13.04 | 0.01+ −0.00 | 59.39 |

TABLE 3

Porcine Growth Hormone Release from Second Control (pure GH Reservoir)

| Time (Days) | Milligrams pGH Released Per Day | Cumulative & pGH Released |
| --- | --- | --- |
| 0.33 | 0.00+ −0.01 | 0.00 |
| 1.04 | 0.35+ −0.11 | 1.23 |
| 2.37 | 0.44+ −0.06 | 4.13 |
| 3.39 | 0.58+ −0.20 | 7.08 |
| 4.38 | 0.74+ −0.19 | 10.70 |
| 5.27 | 0.71+ −0.01 | 13.85 |
| 6.38 | 0.38+ −0.07 | 15.95 |
| 7.31 | 0.24+ −0.15 | 17.05 |

TABLE 3-continued

Porcine Growth Hormone Release from Second Control (pure GH Reservoir)

| Time (Days) | Milligrams pGH Released Per Day | Cumulative & pGH Released |
|---|---|---|
| 8.35 | 0.07+ −0.04 | 17.40 |
| 9.36 | 0.04+ −0.02 | 17.59 |
| 10.37 | 0.03+ −0.02 | 17.72 |
| 11.38 | 0.02+ −0.01 | 17.81 |
| 12.39 | 0.01+ −0.01 | 17.88 |
| 13.36 | 0.01+ −0.00 | 17.92 |

TABLE 4

Sucrose Release from Layered Reservoir Devices

| Time (Days) | Milligrams pGH Released Per Day | Cumulative & pGH Released |
|---|---|---|
| 0.33 | 3.08+ −1.02 | 1.28 |
| 1.04 | 4.12+ −0.32 | 4.93 |
| 2.37 | 3.01+ −2.45 | 9.94 |
| 3.39 | 4.70+ −1.92 | 15.94 |
| 4.38 | 7.52+ −1.76 | 25.21 |
| 5.27 | 5.68+ −0.32 | 31.51 |
| 6.38 | 5.83+ −0.77 | 39.58 |
| 7.31 | 6.49+ −0.57 | 47.11 |
| 8.35 | 5.81+ −0.94 | 54.66 |
| 9.36 | 4.91+ −0.51 | 60.86 |
| 10.37 | 4.71+ −0.22 | 66.86 |
| 11.38 | 4.51+ −0.40 | 72.49 |
| 12.39 | 3.20+ −0.23 | 76.51 |
| 13.36 | 2.38+ −0.34 | 79.39 |

TABLE 5

Sucrose Release from First Control (Homogeneous Reservoir)

| Time (Days) | Milligrams pGH Released Per Day | Cumulative & pGH Released |
|---|---|---|
| 0.39 | 21.35+ −2.32 | 10.41 |
| 1.03 | 21.19+ −4.66 | 27.36 |
| 1.89 | 16.92+ −1.02 | 45.55 |
| 2.89 | 11.06+ −2.03 | 59.38 |
| 3.89 | 8.39+ −1.48 | 69.87 |
| 5.06 | 5.77+ −1.04 | 78.30 |
| 5.86 | 3.45+ −0.42 | 81.75 |
| 6.83 | 2.25+ −0.67 | 84.47 |
| 7.82 | 2.66+ −1.67 | 87.76 |
| 8.82 | 1.24+ −0.88 | 89.31 |
| 10.03 | 0.15+ −0.16 | 89.54 |
| 11.11 | 0.00+ −0.00 | 89.54 |
| 12.06 | 0.00+ −0.00 | 89.54 |
| 13.04 | 0.00+ −0.00 | 89.54 |

EXAMPLE III

Preparation of Extended Delivery Device for Delivery of a Beneficial Agent

A delivery device for the extended delivery of a beneficial agent, such as Parlow porcine growth hormone (see Example I), and a stabilizing agent, such as sucrose, wherein the sucrose is microencapsulated, can be constructed as follows.

Sucrose is microencapsulated in ethylcellulose. The microcapusles range in size from 60 to 150 microns and have a sugar content of about 80%. The sucrose microcapsules and Parlow pGH are thoroughly mixed in a weight ratio of 5:1 using a vortex mixer A 120 mg. portion of the resulting mixture is compressed on a key tablet press equipped with 4-mm. diameter flat-faced punches. The tablet is placed into sterilized pre-cut silicone tubing (Masterflex 6411-165, 3.4 mm. inside diameter) and butted against a microporous polyethylene disc with a pore size of 10 microns, thickness of 2.3 mm. and diameter of 4 mm. A teflon disc then is inserted from the opposite end of the tube and butted against the tablet. Another tablet is inserted into the tube and butted against the teflon disc, followed by another microporous polyethylene disc to produce a releasing device with two releasing ends. Each releasing end then is trimmed with a sterile surgical blade, leaving a recessed end of 1.5 mm.

These devices then may be implanted subcutaneously in swine, where they will release the growth hormone at a substantially steady rate for an extended period of time.

We claim:

1. A device for the continuous administration to a fluid medium of at least two agents having different rates of diffusion, said agents characterized as an agent having a relatively rapid rate of diffusion and an agent having a relatively slow rate of diffusion, which comprises: a wall, formed at least in part by a porous membrane, the remainder of said wall formed by a material impermeable to said agents and to said fluid medium, which completely surrounds and defines a reservoir, the reservoir comprising:

(a) a compartment which comprises said agent having the relatively slow rate of diffusion, wherein said compartment is partly formed by said porous membrane part of said wall permitting said agents to diffuse, and partly formed by a permeable partition, and (b) at least one compartment which comprises said agent having the relatively rapid rate of diffusion, wherein said compartment is not in direct contact with said porous membrane part of said wall, said compartment is in contact with the portion of said wall formed by a material impermeable to said agents and to said fluid medium and is separated by said permeable partition from the compartment comprising said agent having the relatively slow rate of diffusion, such that when said device is exposed to said fluid medium, said agents having different rates of diffusion will diffuse through the porous membrane part of said wall at a substantially steady rate for a prolonged period of time.

2. The device of claim 1 which comprises more than one compartment comprising said relatively rapidly diffusing agent, said compartments separated by said permeable partition form the compartment comprising the agent having the relatively slow rate of diffusion.

3. The device of claim 1 or 2, wherein said compartment comprising said relatively slowly diffusing agent.

4. The device of claim 1 wherein said porous membrane comprises a microporous polyalkylene, a microporous polycarbonate, a microporous polyamide, a microporous modacrylic copolymer, a polyester prepared by esterification of a dicarboxylic acid or anhydride with an alkylene polyol, a phenolic polyester, a crosslinked olefin polymer, a polyolefin, a polyurethane, a polyimide or a polybenzimidazole.

5. The device of claim 4 wherein said porous membrane is a microporous polyalkylene.

6. The device of claim 5 wherein said microporous polyalkylene is microporous polyethylene.

7. The device of claim 1 wherein said impermeable and insoluble portion of said wall comprises an acyl substituted cellulose acetate or alkyl derivative thereof; a partially and completely hydrolyzed alkylene-vinyl acetate copolymer; an unplasticized polyvinyl acetate; a crosslinked homo- or copolymer of polyvinyl acetate; a crosslinked polyester of acryl or methacrylic acid; a polyvinyl alkyl ether, polyvinyl fluoride; silicone; a polycarbonate; polyurethane; a polyamide; a polysulphone; a polyimide; a polyolefin, a polybenzimidazole; a styrene acrlonitrile copolymer; a crosslinked poly(ethylene oxide); a poly(alkylene); poly(vinylimidazole); a poly(ester); a chlorosulphonated polyolefin; or an ethylene-vinyl ester copolymer.

8. The device of claim 7 wherein said impermeable and insoluble portion of said wall comprises silicone.

9. The device of claim 7 wherein said impermeable and insoluble portion of said wall comprises a polyalkylene.

10. The device of claim 9, wherein said polyalkylene is polyethylene.

11. The device of claim 9 wherein said impermeable and insoluble wall portion comprises an ethylene-vinyl ester copolymer.

12. The device of claim 11 wherein said ethylene-vinyl ester copolymer is ethylene-vinyl acetate.

13. The device of claim 1 or 2, wherein said permeable partition or partitions comprises a microporous polyalkylene, a microporous polycarbonate, a microporous polyamide, a microporous modacrylic copolymer, a polyester prepared by esterification of a dicarboxylic acid or anhydride with an alkylene polyol, a phenolic polyester, a cross-linked olefin polymer, a polyolefin, a polyurethane, a polyimide or a polybenzimidazole.

14. The device of claim 13 wherein said permeable partition comprises a microporous polyalkylene.

15. The device of claim 14 wherein said microporous polyalkylene is microporous polyethylene.

16. The device of claim 1 wherein the relatively rapidly diffusing agent and the relatively slowly diffusing agent are each compressed into a pellet before being placed in said reservoir.

17. The device of claim 16 wherein a binder or lubricant is added to the agents before they are compressed into pellets.

18. The device of claim 17 wherein the binder comprises sodium bentonite, ethyl cellulose, stearic acid, calcium stearate, adipic acid, fumaric acid, polyethylene glycol, or cellulose acetate.

19. The device of claim 17 wherein the lubricant comprises magnesium stearate, sodium stearate, calcium stearate, powdered stearate acid, talc, paraffin, cocoa butter, graphite, lycopodium or combinations thereof.

20. The device of claim 1 wherein said relatively slowly diffusing agent is an agent which forms insolubles when it comes in contact with said fluid medium and said relatively slowly diffusing agent stabilizes said relatively slowly diffusing agent.

21. The device of claim 1 wherein at least one of said agent is a beneficial agent.

22. The device of claim 21 wherein both of said agents are beneficial agents.

23. The device of claim 1 which can be orally ingested by a living being.

24. The device of claim 1 which can be implanted into body tissues.

25. The device of claim 1 which can be inserted into a body cavity.

26. The device of claim 1 wherein the fluid medium is a body fluid of a living being and at least one of said agents comprises a drug, vitamin, nutritional supplement, or biologically active protein.

27. The device of claim 26 wherein said drug comprises hypnotics and sedatives, tranquilizers, anticonvulsants, muscle relaxants, analgesics, antiinflammatory agents, local anesthetics, antimicrobials, androgenic, progestational and estrogenic steroids, sympathomimetric drugs and diruetics.

28. The device of claim 26 wherein said relatively slowly diffusing agent is a biologically active protein.

29. The device of claim 25 wherein said protein is an animal growth hormone and said relatively rapidly diffusing agent is a compound which stabilizes said growth hormone.

30. The device of claim 29 wherein said growth hormone is bovine growth hormone.

31. The device of claim 29 wherein said growth hormone is ovine growth hormone.

32. The device of claim 29 wherein said growth hormone is avian growth hormone.

33. The device of claim 29 wherein said growth hormone is porcine growth hormone.

34. The device of claim 29 wherein said stabilizer comprises sucrose, sorbitol, disaccharides, glycine, glycine HCl or alanine.

35. A method for continuously administering in a fluid medium a diffusible agent having a relatively rapid rate of diffusion and an agent having a relatively slow rate of diffusion which comprises placing the device of claim 1 in the fluid medium.

36. The method of claim 35 wherein the fluid medium is a body fluid of a living being.

37. A method for continuously administering in a fluid medium a diffusible agent having a relatively rapid rate of diffusion and an agent having a relatively slow rate of diffusion which comprises placing the device of claim 2 in the fluid medium.

38. A method for continuously administering in a fluid medium a diffusible agent having a relatively rapid rate of diffusion and an agent having a relatively slow rate of diffusion which comprises placing the device of claim 3 in the fluid medium.

* * * * *

UNITED STATES PATENT AND TRADEMARK OFFICE
CERTIFICATE OF CORRECTION

PATENT NO. : 5,008,112

DATED : April 16, 1991

INVENTOR(S) : Randolph B. DePrince and Ravi Viswanathan

It is certified that error appears in the above-identified patent and that said Letters Patent is hereby corrected as shown below:

Title Page:

In the Abstract, line 4, "show" should read --slow--

Column 3, line 45, "sucrose" second occurrence, should read --sucrose.--

Column 5, line 12, "prolonger" should read --prolonged--

Column 13, line 62, "mixer" should read --mixer.--

Column 14, Claim 3, "The device of claim 1 or 2, wherein said compartment comprising said relatively slowly diffusing agent." should read --The device of claim 1 or 2, wherein said compartment comprising said relatively slowly releasing agent additionally comprises a relatively rapidly diffusing agent.--

Signed and Sealed this

Twenty-fifth Day of August, 1992

Attest:

DOUGLAS B. COMER

Attesting Officer

Acting Commissioner of Patents and Trademarks